United States Patent [19]

Halfman

[11] Patent Number: 4,640,898
[45] Date of Patent: Feb. 3, 1987

[54] HOMOGENEOUS FLUORESCENCE LIGAND BINDING ASSAY BASED UPON PREFERENTIAL ALTERATION OF THE RESPECTIVE INTENSITIES OF BOUND AND FREE LABEL BY SOLVENT COMPONENTS

[75] Inventor: Clarke J. Halfman, Highland Park, Ill.

[73] Assignee: University of Health Sciences/The Chicago Medical School, North Chicago, Ill.

[21] Appl. No.: 518,965

[22] Filed: Aug. 1, 1983

[51] Int. Cl.⁴ .............................. G01N 33/533
[52] U.S. Cl. ...................... 436/546; 436/501; 436/537; 436/800; 436/826; 436/829
[58] Field of Search ........ 436/501, 503, 505, 536–537, 436/800, 808–810, 815, 826, 829, 546; 435/4, 7

[56] References Cited

U.S. PATENT DOCUMENTS

| | | | |
|---|---|---|---|
| 3,971,952 | 7/1976 | Inbar | 250/461.2 |
| 4,071,770 | 1/1978 | Shinitzky et al. | 250/302 |
| 4,122,348 | 10/1978 | Bruck | 250/461.2 |
| 4,131,800 | 12/1978 | Bruck et al. | 250/461.2 |
| 4,193,983 | 5/1980 | Ullman | 436/819 |
| 4,255,411 | 3/1981 | Lim et al. | 436/815 |
| 4,257,676 | 3/1981 | Greubel et al. | 136/247 |
| 4,260,219 | 4/1981 | Greubel et al. | 350/96.1 |
| 4,374,925 | 2/1983 | Litman | 436/800 |
| 4,483,921 | 11/1984 | Cole | 436/537 |
| 4,492,762 | 1/1985 | Wang et al. | 436/537 |
| 4,495,293 | 1/1985 | Shaffar | 436/800 |

OTHER PUBLICATIONS

Halfman, Clarke J. et al., Analytical Chemistry, 57:1928–1930 (1985).
Halfman, C. J. et al., Anal. Chem., vol. 56(9), pp. 1648–1650 (1984).
Halfman, C. J. et al., Anal. Chem., vol. 54(12), pp. 2009–2011 (1982).
Halfman, C. J. et al., Biochem., vol. 11(18), pp. 3493–3498 (1972).
Hirota, S. et al., Mukog, Joshi Paig. Kujo, vol. 30, H53–H59 (1982), CA99 (18):141526g Abstract.
Tsuchiya, S. et al., J. Amer. Chem. Society, vol. 103(24), pp. 7370–7371 (1981), CA 95(24):212248y.
Henglein, A. et al., Ber. Bunsen. Phys. Chem., vol. 82(10), pp. 1107–1112 (1978), CA 89(26):223446p.
Correll, G. D. et al. J. Amer. Chem. Soc., vol. 100(4), 1254–1262 (1978), CA 89(7):59340b.
Kohara, H. et al., Kitak. Kogyo Koto Semmon Gakko Kenkyu Hokoku, vol. 10, pp. 9–13 (1977).
Lakowicz, J. R. et al., J. Biol. Chem., vol. 258(9), pp. 5519–5524 (1983), Biosis Abstract 76077425.
Guha, S. N. et al., Proc. Indian Acad. Sci. Chem. Sci., vol. 91(1), pp. 73–86 (1982), Biosis Abstract 75015871.
Halfman, C. J. et al., Biochem. Biophys. Acta, vol. 243, pp. 284–293, 294–303 (1971).

Primary Examiner—Charles F. Warren
Assistant Examiner—M. Moskowitz
Attorney, Agent, or Firm—Norman Lettvin

[57] ABSTRACT

Fluorescence ligand binding assay of a sample containing an unknown amount of ligand may be performed by making direct intensity measurements. In an immunoassay, for example, the sample may be added to a solution containing fluorescein labeled analyte and then is added an antibody specific to the analyte. Sodium dodecyl sulfate, a surfactant, added to the solution in an amount sufficient to form micelles provides markedly different fluorescent intensity from bound and unbound labeled analyte.

1 Claim, 2 Drawing Figures

HOMOGENEOUS FLUORESCENCE LIGAND BINDING ASSAY BASED UPON PREFERENTIAL ALTERATION OF THE RESPECTIVE INTENSITIES OF BOUND AND FREE LABEL BY SOLVENT COMPONENTS

FIELD OF THE INVENTION

This invention relates to an improved method and composition for fluorescence ligand binding assays, and, in particular, immunoassays.

BACKGROUND OF THE INVENTION

A ligand binding assay is an analytical technique for measuring concentrations of substances that react selectively with specific binding proteins. Such substances are generally called ligands in the field of biochemistry. Immunoassays to measure concentrations of antigens that react selectively with specific antibodies comprise a class of ligand binding assays.

Assay reagents in a ligand binding assay generally include:

1. A specific binding protein such as an antibody (Aby) that specifically and strongly binds the substance to be measured, referred to as the analyte (A), the strong binding being characterized by an equilibrium dissociation constant less than about $10^{-8}$M; and
2. Labeled analyte (A.L).

The label (L) provides a measurable property of the system for the purpose of monitoring the extent of binding of A.L to Aby in a solution.

The basic assay principle is illustrated by the equilibrium relationship

$$A.L + A - Aby \rightleftharpoons A.L + Aby + A \rightleftharpoons A.L - Aby + A \quad (1)$$

where the hyphen indicates binding. Thus, in accordance with Eq. (1), A and A.L compete for binding to Aby. The more A present in a solution containing A.L and Aby, the less A.L will be bound to Aby. An assay is conducted by adding a sample containing an unknown amount of A to a solution which contains a known concentration of A.L. A measured amount of Aby is then added. The amount of A in the sample may be deduced by measurement of the concentration of bound A.L.

Radioactivity is a known label employed in immunoassays. Use of radioactive labels, however, requires physical separation of bound and free labeled analyte by procedures involving protein precipitation or removal of free label with particulate adsorbents. The separation procedures are time-consuming and contribute significantly to assay imprecision.

Since the inception of radioimmunoassay about twenty years ago, other labels have come into use. Some of the more recent labels have the desirable characteristic of having a measurable property that is significantly different for bound and free labeled analytes so that physical separation is unnecessary. Assays not requiring separation are known as "homogeneous".

Fluorescent dyes have been shown to be useful as labels in homogeneous immunoassays as described in J. F. Burd, "Fluoroimmunoassays in Drug Monitoring", *Clinical Chemistry News* (April 1982), p. 33. The lifetime of the excited state and the rate of rotary motion of a dye molecule is such that the polarization of free labeled analyte is low, and the polarization of labeled analyte bound to a large protein is high. Fluorescence polarization is accordingly known to be a useful response variable as described in M. E. Jolley, et. al., "Fluorescence Polarization Immunoassay I", *Clinical Chemistry* 27 (1981), p. 1190. Determination of polarization requires measurement of two intensities and the use of polarizers in the excitation and detection beams with consequent reduction in signal intensity by about a factor of 10. Polarization immunoassay also requires a specially designed fluorometer, which is expensive.

Measurement of intensity differences is simpler and potentially more sensitive than polarization measurements. Significant intensity differences between bound and free labeled analyte, however, do not generally occur. Only in the case of thyroxin, as the analyte, has the intensity of the bound label been found to be significantly different (3x) from that of the free label, as shown in D. S. Smith, "Enhancement Fluoroimmunoassay of Thyroxine," *FEBS Letters* 77 (1977) p. 25. An intensity difference of 20% between bound and free fluorescein labeled gentamicin has been reported in E. J. Shaw, et al., "Estimation of Serum Gentamicin by Quenching Fluorimmunoassay," *Journal of Clinical Pathology* 30 (1977) p. b 526, to serve as the basis of a homogeneous response variable. The Shaw, et al. measurements required subtraction of fluorescent background from control samples containing antibody. The magnitude of the background subtraction was comparable to the intensity difference measured, thereby limiting the precision with which gentamicin concentration could be determined.

Because of the potential advantages of intensity measurements, efforts have been directed toward developing methods that would cause the intensity of free and bound label to differ more markedly. One known method is based upon the phenomenon of excitation energy transfer and requires conjugation of a complementary acceptor dye to the antibody as described in E. F. Ullman, et al., "Fluorescent Excitation Transfer Immunoassay," *Journal of Biological Chemistry* 251 (1976) p. 4172. When two dyes, with properly matched spectral properties, are sufficiently proximate, the excitation energy of the donor dye is transferred to the acceptor dye. If the acceptor dye is nonfluorescent, then the energy transfer results in reduced fluorescence intensity. The distance across which the energy can be effectively transferred from one dye to the other is such that labeled analyte must be bound to the antibody which has been conjugated with the acceptor dye. Therefore, bound labeled analyte is preferentially quenched and free labeled analyte is fully fluorescent. A disadvantage of this method is the need to conjugate acceptor dye to the antibody. Also, the amount of acceptor dye conjugation must be large enough to assure proximity to the binding site which is located at one end of a relatively large, elongated protein. On the other hand the amount of conjugation must not be so large that the binding affinity of the chemically altered antibody is substantially reduced. As a result, the criticality of the acceptor dye conjugation makes the dye-antibody conjugate difficult to manufacture and makes the excitation energy method expensive.

Another known method involves the use of an additional antibody generated against the label, as described in R. F. Zuk, "Fluorescence Protection Immunoassay," *Clinical Chemistry* 25 (1979) p. 1554. When some dye labels are bound to their antibodies, they no longer fluoresce. Furthermore, some such labels can bind to their antibodies only when free. Thus the free label is preferentially quenched because the dye moieties of the labeled analyte bound to the analyte antibody cannot bind to the label antibody. A disadvantage of this system is the need for an additional antibody which is expensive.

Accordingly, there is need for a simple and inexpensive ligand binding assay method using a nonprotein solute for preferentially altering the relative intensities of bound and free labels. The assay method should preferably be substantially independent of the particular ligand to be assayed.

SUMMARY OF THE INVENTION

A feature of a preferred embodiment exemplifying the present invention is the use of micelles to sequester bound from free labeled analyte. The sequestration provides different environments for the bound and free labels with a resultant difference in fluorescent characteristics.

Micelles are aggregates of particles of colloidal dimensions formed by surfactants, otherwise known as detergents, when dissolved above a critical concentration in water. Interactions between micelles and fluorescent dyes have been the subject of intensive investigations, reviewed by M. Graetzel, et al., in "The Application of Fluorescence Techniques to the Study of Micellar Systems," in E. L. Wehry, Ed., *Modern FLuorescence Spectroscopy* 2, New York, Plenum Press, 1976, incorporated herein by reference. As described by Graetzel, et al., a micelle may be a spherical structure having a radius of about 10–28 Å. The interior is normally water excluding, or hydrophobic, whereas the exterior surface is hydrophilic and is in contact with the bulk water.

Fluorescent yield and degree of fluorescent polarization of certain dyes are very sensitive to the presence of micellar aggregates. The sensitivity for some dyes arises from the adsorption of the dye polar groups on the surface of the micelles. The sensitivity for other dyes arises from the capture of the dye molecule into the hydrophobic interior of the micelles. The capture accordingly sequesters the dye molecule from its aqueous environment.

It has been discovered in connection with experiments leading to the present invention that dye-labeled analytes also interact with micelles when free but not when bound to antibody.

As a result, the free and bound labeled analyte, when present in a solution containing micelles, will have different fluorescent characteristics.

On the other hand the differential effect of surfactant upon the fluorescent characteristics of free and bound labeled analyte is expected to be substantially insensitive to the choice of analyte. That is, for a large number of analytes it will be the dye properties that predominantly determine any free-bound differences and the effect of the analyte will be relatively unimportant. Embodiments of the present invention may accordingly be of substantially general application.

A method for fluorescent ligand binding assay exemplifying principles related to the present invention may be used to analyze a sample containing an unknown amount of a specified analyte. The method makes use of a prepared amount of the same analyte labeled with a suitable fluorescent dye. A measured amount of the sample together with a predetermined amount of the labeled analyte is placed in an aqueous solution to which is added a predetermined amount of antibody. A surfactant is also added to the solution in an amount greater than the threshold amount necessary to cause the surfactant to form micelles in the solution. Fluorescent emission from the solution is then measured. In one embodiment the surfactant preferentially quenches the emission from free labeled analyte to effect a homogeneous response. Measurement of the intensity of the fluorescence of the solution accordingly provides a measure of the fraction of labeled analyte which has been bound by the antibody in the solution, as may be inferred from Eq. (1).

Not every fluorescent dye is suitable for use with every surfactant. It is necessary that the surfactant-dye combination be selected so that the surfactant is operative to effect different fluorescent intensities between bound and free labeled analyte. Such differential effects may generally be expected to occur when micelles are operative to sequester the free from the bound labeled analytes and maintain them in different environments.

An object of this invention, accordingly, is to provide an improved method for assaying the concentration of an analyte in a solution by measuring the intensity of fluorescence of labeled analyte in the solution.

Another object of this invention is to provide a composition including a sequestering solute such as a surfactant for use in immunoassay to effect a preferential quenching of either the bound or free labeled analyte in a solution containing protein that binds specifically and strongly to the analyte.

These and other objects, advantages and features of the invention, as well as many of the particular advantages, become readily apparent from the following detailed description which is presented in conjunction with the accompanying drawings.

DETAILED DESCRIPTION OF A PREFERRED EMBODIMENT

A gentamicin immunoassay provides an example of a preferred embodiment according to principles derived from the present invention. The embodiment uses the surfactant sodium dodecyl sulphate (SDS) which is suitable for use with the dye fluorescein. A reactive derivative of fluorescein may be used to label gentamicin to make a fluorescein conjugate. Gentamicin antibody may also be prepared as described, for example in E. J. Shaw, et al., included herein by reference. Accordingly, a measured amount of a sample containing an unknown amount of gentamicin, a predetermined amount of conjugate, a predetermined amount of gentamicin antibody and sufficient SDS to form micelles are prepared in a buffered solution. Fluorescent emission from the solution may then be compared with the fluorescent emission from solutions that are similar except for the presence of known amounts of unlabeled gentamicin instead of the sample. The comparison of intensities thereby permits the amount of gentamicin in the sample to be determined.

It may accordingly be seen that a general method for fluorescence ligand binding assay of a sample containing an unknown amount of an analyte may comprise the steps of: preparing a protein that specifically and strongly binds to the analyte, preparing a conjugate including the analyte and a fluorescent dye, preparing an aqueous solution containing a measured amount of the sample, a predetermined amount of the conjugate, the protein and a surfactant, the surfactant concentration being greater than the micelle threshold, and measuring the intensity of fluorescent emission from the solution, the dye and detergent being operative to effect differential fluorescent intensity between bound conjugate and free conjugate.

The embodiment may be better understood by considering the exemplary immunoassay in more detail.

Labeled gentamicin is prepared for assay use by combining a dichlorotriazin derivative of fluorescein with gentamicin, as described in Jolley, et al., p. 1190. Antibody that specifically and strongly binds to gentamicin is similarly prepared in a buffered solution (0.01M sodium phosphate and 0.15M sodium chloride, pH=7.4) at a predetermined concentration.

Also, several different concentrations of gentamicin reference solution in buffer are prepared in order to provide a range of standards. Correspondingly, the sample with an unknown amount of gentamicin is also prepared in the same buffered solution.

Figure 1:
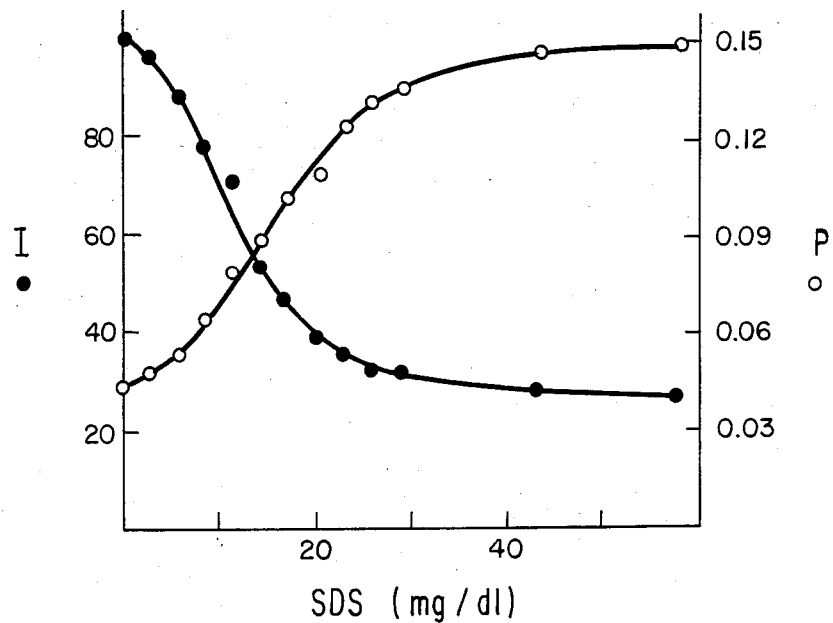
FIG. 1 illustrates the effect of sodium dodecyl sulphate (SDS) in solutions containing gentamicin labeled with fluorescein upon the intensity and polarization of the fluorescence.
Figure 2:
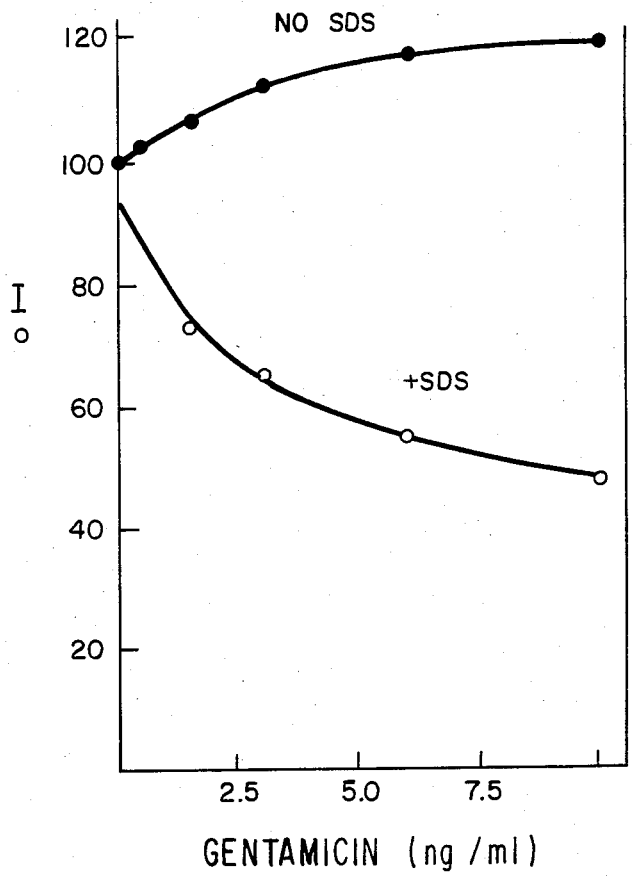
FIG. 2 illustrates the effect of SDS quenching upon the fluorescence intensity of fluorescein labeled gentamicin in a solution containing gentamicin antibody as a function of unlabeled gentamicin concentration compared with the intensity from a similar solution without SDS.

Aliquots of the different standard solutions are respectively pipetted into different standard tubes, such as test tubes. An equal amount of sample solution is pipetted into a sample tube. Equal predetermined amounts of labeled gentamicin solution are also added to the respective standard and sample tubes. After mixing, equal amounts of antibody solution are added to the respective tubes, mixed, and the tubes incubated. Just prior to measurement of fluorescent intensity equal amounts of SDS in buffered solution are added to each tube. The fluorecent intensity of the standards are then measured and plotted as in FIG. 2. The fluorescent intensity of the sample may then be used to determine the sample gentamicin concentration by interpolation.

The SDS in buffered solution is prepared at a concentration sufficiently high so that the SDS concentrations in the tubes is above the micelle threshold. Assay concentrations of labeled gentamicin and antibody are adjusted to have a midrange intensity response at a useful analyte concentration.

Table I summarizes an experimental determination of gentamicin concentrations in commercial control samples. Standards and samples in volumes of 20 μl and 1:10 dilution are added to the respective tubes. Next, 40 μl of 100 nM fluorescein labeled gentamicin is added to each tube and the tube contents mixed. After mixing, 40 μl of gentamicin antibody is added to each tube and the tube contents are mixed again. All reagents mentioned are from an immunoassay kit which is commercially available from Abbott Laboratories, Inc., North Chicago, IL. After a few minutes for incubation SDS solution in amounts of 2 ml at 50 mg/dl concentration is added to each tube and the fluorescent intensity measured at 520 nm emission wave length with an excitation wave length of about 490 nm. The intensity of the standards is plotted and the sample concentrations determined by interpolation from the resulting curve.

TABLE I

| Tube # | Identity | Intensity (Relative Units) | sample results |
|---|---|---|---|
| | Standards | | |
| 0 | 0.0 μg/ml | 100 | |
| 1 | 0.5 μg/ml | 96 | |
| 2 | 1.5 μg/ml | 82 | |
| 3 | 3.0 μg/ml | 62 | |
| 4 | 6.0 μg/ml | 52 | |
| 5 | 10.0 μg/ml | 47 | |
| | Samples | | |
| 6 | #1 specimens | 86 | 1.1 μg/ml |
| 7 | #2 20 μl of 1:10 | 59 | 3.7 μg/ml |
| 8 | #3 dilutions | 50 | 7.6 μg/ml |

The uncertainties in the determinations of the sample concentrations are presently undetermined but are believed to be in the 5%–10% range.

It is presently desirable and convenient to prepare a response curve, as described, for each batch of reagents. Response curves may vary significantly from one batch to another because of variations in antibody binding strengths, even within a single batch, when antibodies are generated from an immune response. It is to be expected that in the future, however, there will be more use made of monoclonal antibodies or other homogeneous binding proteins, in which case response curves may be standardized or readily calculated.

It will, of course, be understood that modification of the present invention in its various aspects will be apparent to those skilled in the art, some being apparent only after study and others being a matter of routine design. For example, ligands other than gentamicin and dyes other than fluorescein may be used in connection with the invention. Also, the use of a micelle forming surfactant is not a necessary feature of the invention but other nonprotein sequestering solutes which provide different environments within a solvent for, respectively, bound and free labeled analytes to cause them to fluoresce differently may do just as well. Furthermore, other nonprotein solutes that cause differential fluorescence affects also fall within the bounds of the present invention. As such, the scope of the invention should not be limited by the particular method and combination herein described but should be defined only by the appended claims and equivalents thereof.

What is claimed is:

1. A method for conducting a ligand binding assay to determine the concentration of an analyte in a sample containing an unknown amount of the analyte comprising the steps of:
    preparing an aqueous solution containing the sample, a conjugate comprising the analyte and the fluorescent dye fluorescein, a protein that binds specifically and strongly to the analyte, and the surfactant, sodium dodecyle sulphate, having a micelle threshold, the surfactant concentration being greater than said micelle threshold; and
    measuring the intensity of fluorescent emission from said solution while irradiating said solution with electromagnetic radiation;
    said surfactant effecting different fluorescence intensities from bound conjugate and from free conjugate.

* * * * *